United States Patent
Ohyama et al.

(10) Patent No.: US 6,918,909 B2
(45) Date of Patent: Jul. 19, 2005

(54) RESECTOSCOPE APPARATUS

(75) Inventors: Masahide Ohyama, Hino (JP); Kazuya Hijii, Tama (JP); Shinji Hatta, Hachioji (JP); Kenji Harano, Hachioji (JP); Takeaki Nakamura, Hino (JP); Shuichi Kimura, Hachioji (JP)

(73) Assignee: Olympus Corporation, Tokyo (JP)

(*) Notice: Subject to any disclaimer, the term of this patent is extended or adjusted under 35 U.S.C. 154(b) by 82 days.

(21) Appl. No.: 10/410,702

(22) Filed: Apr. 10, 2003

(65) Prior Publication Data
US 2004/0082938 A1 Apr. 29, 2004

(30) Foreign Application Priority Data

Apr. 10, 2002 (JP) ........................................ 2002-108208
Apr. 15, 2002 (JP) ........................................ 2002-112396

(51) Int. Cl.[7] ............................................. A61B 18/18
(52) U.S. Cl. ............................................ 606/46; 606/48
(58) Field of Search ..................................... 606/46, 48

(56) References Cited

U.S. PATENT DOCUMENTS 5,112,330 A * 5/1992 Nishigaki et al. ........... 600/143
5,807,240 A * 9/1998 Muller et al. ................ 600/135
6,004,319 A   12/1999 Goble et al.
6,113,597 A * 9/2000 Eggers et al. ................. 606/46
6,322,494 B1 * 11/2001 Bullivant et al. ............ 600/104

FOREIGN PATENT DOCUMENTS

JP   2000-201946    7/2000

* cited by examiner

Primary Examiner—Beverly M. Flanagan
Assistant Examiner—Matthew J Kasztejna
(74) Attorney, Agent, or Firm—Scully, Scott, Murphy & Presser

(57) ABSTRACT

A resectoscope apparatus includes a high-frequency generating device which generates high-frequency current, a hollow sheath which can be inserted in the celom, a scope which is arranged in the sheath and which can observe the celom, an active electrode which transmits the high-frequency current to the body organ, and a solution supply device which supplies a solution to the hollow sheath. At least one of the sheath and the scope has conductivity. The sheath or the scope having the conductivity is connected to high frequency generating device via a connecting member so as to collect return current.

8 Claims, 16 Drawing Sheets

RESECTOSCOPE APPARATUS

This application claims benefits of Japanese Application Nos. 2002-108208 filed on Apr. 10, 2002, and 2002-112396 filed on Apr. 15, 2002, the contents of which are incorporated by this reference.

BACKGROUND OF THE INVENTION

1. Field of the Invention

The present invention relates to a resectoscope apparatus which incises, resects, and transpires the body tissue through electric resection under an endoscope.

2. Description of the Related Art

Generally, a resectoscope is used for transurethral resection (TUR) and transcervical resection (TCR), and mainly comprises an optical scope (also referred to as a scope) as an endoscope for observation and an electrode unit for resecting the organ in an elongated and hollow sheath inserted in the celom.

The resectoscope apparatus includes two types of one for treatment in a non-conductive solution and one for treatment in a conductive solution.

Upon treatment such as the prostatectomy by using the resectoscope apparatus for treatment in the non-conductive solution, the space is expanded by supplying D-sorbitol as an insulative transparent solution corresponding to perfusate for expanding the narrow space and the sheath of the resectoscope is inserted into the space.

High-frequency current is energized to a treatment electrode of the electrode unit arranged to the opening of a distal end portion of the sheath while observing a surface of the lesion portion by using the resectoscope arranged in the sheath.

The high-frequency current flows to a counter-electrode plate as an external electrode arranged to the outside of the body via the body organ from the treatment electrode. An operator advances or retracts the treatment electrode by operating an operating unit for the treatment of the lesion portion.

In the case of the prostatectomy by using the resectoscope apparatus for treatment in the conductive solution, physiological saline or the like is used for the perfusate as the conductive solution. In the technology disclosed in Japanese Unexamined Patent Application Publication No. 2000-201946, a return electrode is arranged near the distal end portion of the elongated and hollow sheath inserted in the celom filled with a conductive solution and the high-frequency current from the treatment electrode is collected via the return electrode.

SUMMARY OF THE INVENTION

According to the present invention, a resectoscope apparatus comprises a high-frequency generating device which generates high-frequency current, a hollow sheath which can be inserted in the celom, a scope which is arranged in the sheath and which can observe the celom, an active electrode which transmits the high-frequency current to the body organ, a solution supply device which supplies a solution to the hollow sheath, and a connecting member for connection to the high frequency generating device which uses at least one having conductivity, of the sheath and the scope as a member for collecting return current.

BRIEF DESCRIPTION OF THE DRAWINGS

FIGS. 1 to 14 are diagrams according to a first embodiment of the present invention, in which:

FIG. 1 is a diagram showing the structure of a resectoscope apparatus according to the first embodiment;

FIG. 2 is a side view showing the structure of a resectoscope;

FIG. 3 is a perspective view for explaining the structure of an electrode;

FIG. 4 is an assembly diagram for explaining the structure of the resectoscope;

FIG. 5 is a block diagram showing the structure of a high-frequency power supply device;

FIG. 6 is a side view showing the structure of the resectoscope having a connector for connection to a cable for return current at a proximal portion of an outer sheath;

FIG. 7 is a side view showing the structure of a resectoscope having a connector for connection to a cable for return current at a proximal portion of an inner sheath according to a first modification thereof;

FIG. 8 is a side view showing the structure of a resectoscope having a connector for connection to the cable for the return current at a proximal portion of a scope according to a second modification thereof;

FIG. 9 is a side view showing the structure of a resectoscope having a connector for connection to the cable for the return current at a handle portion according to a third modification thereof;

FIG. 10 is a side view showing the structure for supplying and collecting active current and the return current by each of the cables in a single cable thereof according to the third modification;

FIG. 11 is a side view showing the structure of a resectoscope having the connector for connection to the cable for the return current at one end of a fluid tube according to a fourth modification thereof;

FIG. 12 is a side view showing the structure in which the connector is projected from a side portion of the fluid tube according to the fourth modification;

FIG. 13 is an explanatory diagram showing a status of the treatment by adhesion of a counter-electrode plate to the patient body;

FIG. 14 is a diagram showing the structure in which a conductive balloon is arranged to the outer periphery of an inserting portion and the adhesiveness to the body organ of the celom is improved;

FIGS. 15 to 17 are diagrams according to a second embodiment of the present invention, in which:

FIG. 15 is a diagram showing the structure of a resectoscope apparatus according to the second embodiment;

FIG. 16 is a block diagram showing the structure of high-frequency power supply shown in FIG. 15; and FIG. 17 is a diagram showing output characteristics of a first output transformer circuit and a second output transformer circuit shown in FIG. 16.

DETAILED DESCRIPTION OF THE PREFERRED EMBODIMENTS

Hereinbelow, a description is given of embodiments of the present invention with reference to the drawings.

A description is given of the structure of a resectoscope apparatus according to a first embodiment of the present invention with reference to FIGS. 1 to 14.

Figure 1:
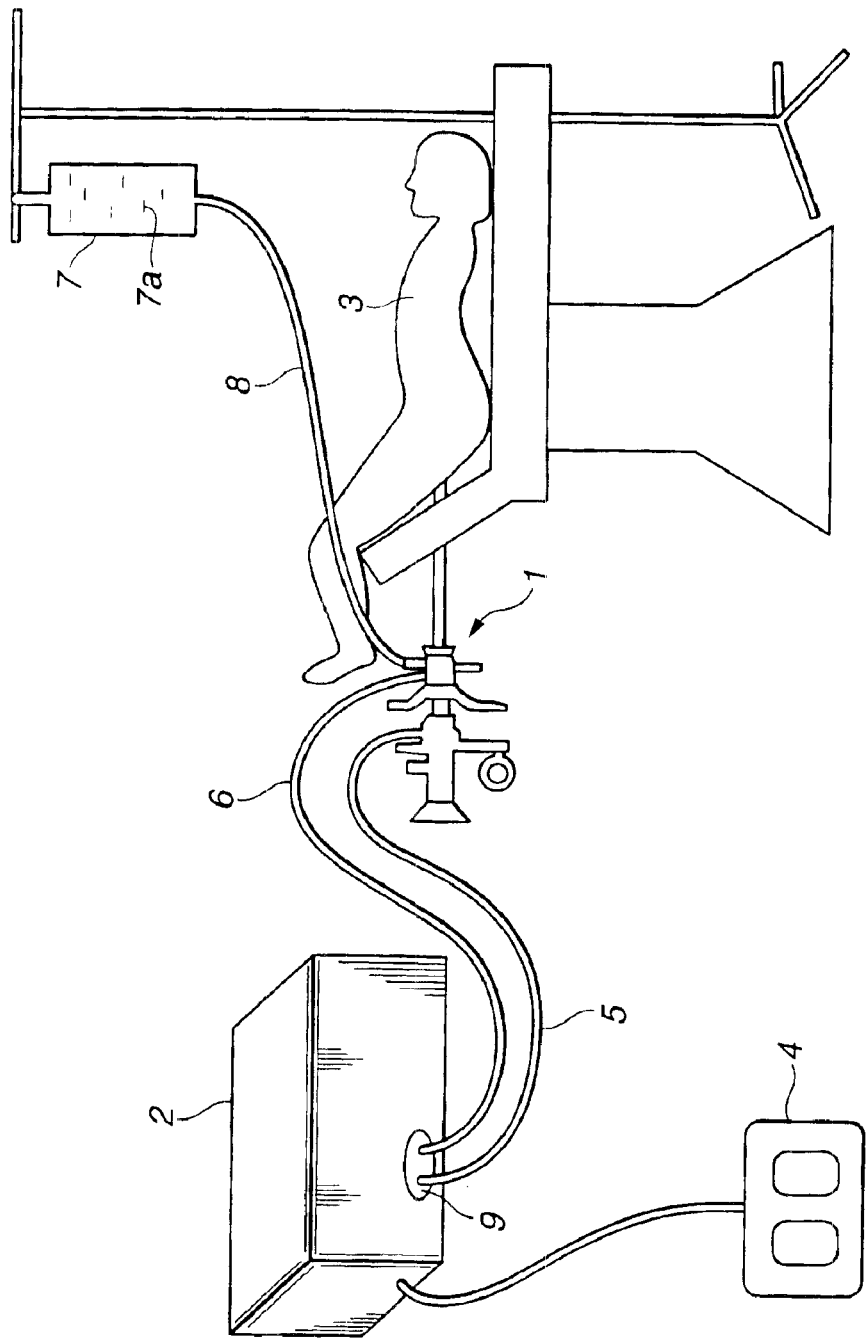

FIG. 1 shows a status for transurethral resection using the resectoscope apparatus as an electric operation device. The resectoscope apparatus comprises a resectoscope 1 and a high-frequency power supply device 2. The resectoscope 1 is connected to the high-frequency power supply device 2 which supplies a high-frequency cautery current (hereinafter, referred to as active current) and which collects feedback current (hereinafter, referred to as return current), to/from a treatment electrode of an electrode unit which will be described later.

A distal end portion of the resectoscope 1 is transurethrally inserted in a patient 3. A foot switch 4 is switched on or off to control the power supply to the treatment electrode from the high-frequency power supply device 2. The foot switch 4 is turned on and thus the high-frequency current from the high-frequency power supply device 2 is supplied to the treatment electrode of the resectoscope 1 via a cable 5 having a connector 9 which is detachably connected to a connector supporter of the high-frequency power supply device 2. As will be described later, the return current is collected to the high-frequency power supply device 2 via the connector supporter to which the connector 9 at the base end is connected via the cable 6.

Referring to FIG. 1, physiological saline 7a with conductivity as perfusate to the celom such as the bladder is supplied to the resectoscope 1 from a physiological saline pack 7 via a sterilizing tube 8.

The operator fills the celom with the physiological saline 7a, then inserts the resectoscope 1 to the celom, moves the treatment electrode to the surface of the body organ for the incision and resection while viewing the endoscope image for observing the celom, and turns on a switch of the foot switch 4 for the incision.

Figure 2:
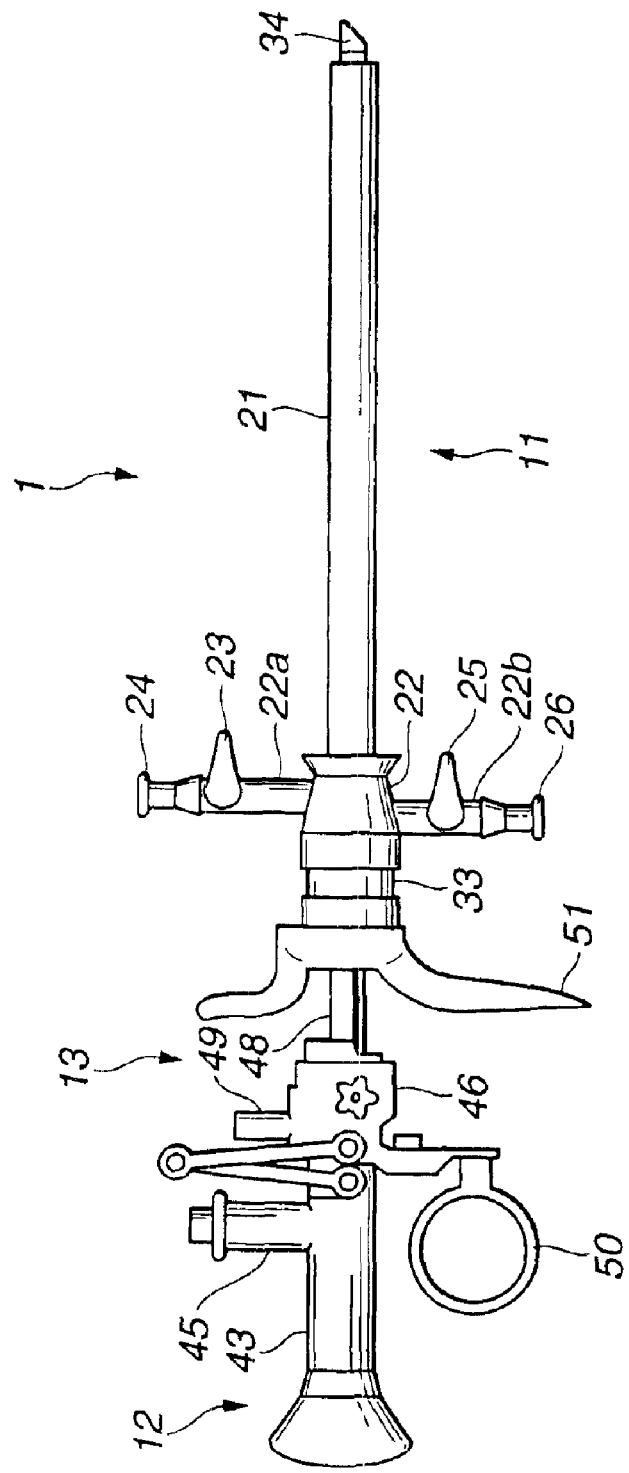
Figure 3:
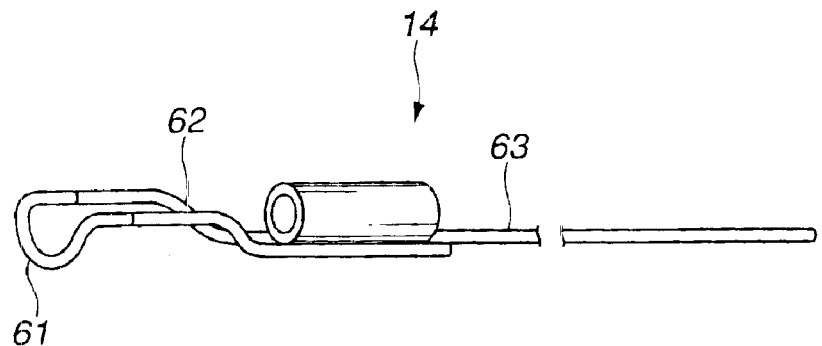
Figure 4:
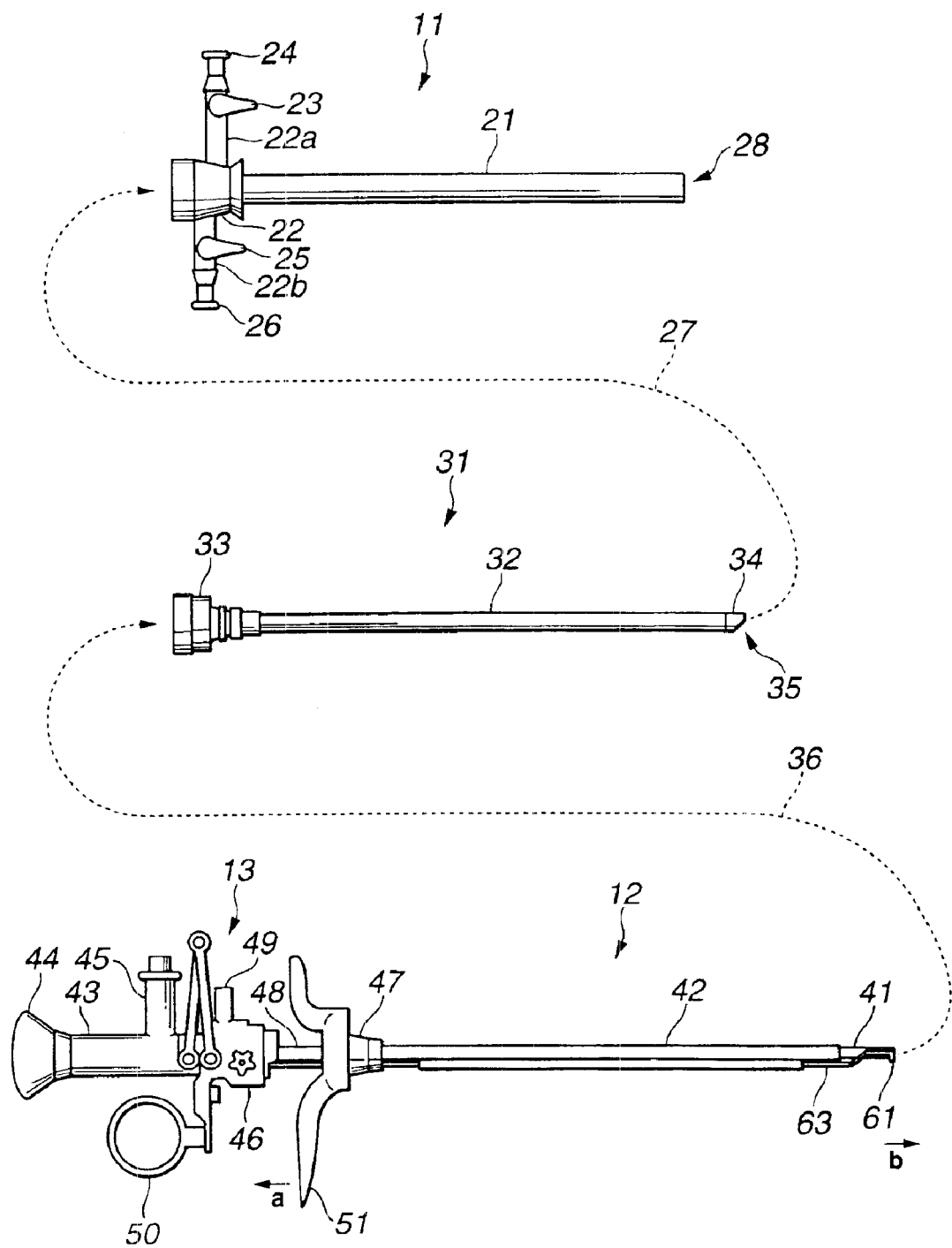

The structure of the resectoscope 1 will be described with reference to FIGS. 2 to 4. FIG. 2 is a side view showing the structure of the resectoscope 1. FIG. 3 is a perspective view for explaining the structure of the treatment electrode. FIG. 4 is an assembly diagram for explaining the structure of the resectoscope 1.

The resectoscope 1 comprises a hollow outer sheath 11 having a piercing hole as a mantle tube, a scope 12 arranged in the piercing hole of the outer sheath 11, for obtaining the endoscope image for observation, a handle portion 13 as an operating portion, and an electrode unit 14 arranged in the piercing hole of the outer sheath 11.

The outer sheath 11 comprises a hollow inserting portion 21 which is inserted in the celom via the urethra, and a proximal main body portion 22 arranged to the rear end of the inserting portion 21. The distal end of the inserting portion 21 has an opening portion 28.

The proximal main body portion 22 has two fluid tubes 22a and 22b at the side periphery thereof. Specifically, the fluid tube 22a comprises a cock 23 and a solution supply cap 24 which transmit the physiological saline or the like with the conductivity as the perfusate to the treatment portion.

The fluid tube 22b comprises a cock 25 and a solution drain cap 26 which drain the physiological saline or the like. A tube for transmitting the solution is connected to the solution supply cap 24 forming tube connecting means. A tube for draining the solution is connected to the solution drain cap 26 forming the tube connecting means. The solution transmission and the solution drain are controlled by moving the cocks 23 and 25.

An inner sheath 31 is inserted from the opening portion of the proximal main body portion 22 on the rear side thereof as shown by a dotted line 27 in FIG. 4 and is arranged in the inserting portion 21. The inner sheath 31 comprises a hollow inserting portion 32 which is inserted in the outer sheath 11, a proximal main body portion 33 arranged to the rear end of the inserting portion 32, and a distal end member 34 which is arranged to the distal end of the inserting portion 32 and which is made of a hard resin member as an insulating member.

The distal end member 34 comprises an opening portion 35 at the distal end thereof. As shown by a dotted line 36 in FIG. 4, the scope 12 is inserted from the opening portion of the proximal main body portion 33 on the rear side thereof, together with the electrode unit 14, and is arranged in the inner sheath 31.

Incidentally, only the inner sheath 31 is attached and used, without using the outer sheath 11.

The scope 12 comprises a hard inserting tube 41 which is inserted and arranged into the elongated inner sheath 31 incorporating an observation optical system, a guide tube 42 to which the inserting tube 41 is inserted, and a proximal portion 43 which is arranged to the base end of the guide tube 42. The proximal portion 43 comprises an ocular portion 44 for operator's visually viewing operation at the base end of the proximal portion 43. The proximal portion 43 comprises, at the side portion thereof, a light guide connecting portion 45 to which a light guide (not shown) for supplying illumination light for observation to an observing portion is connected.

Referring to FIG. 3, the electrode unit 14 inserted and arranged in the inner sheath 31 mainly comprises a treatment electrode 61 arranged to the distal end side and made of a hard metal member, a bifurcating arm member 62 which is continuously arranged and bifurcated to the base end of the treatment electrode 61, and an elongated metal pipe 63 which is extended from a proximal portion of the bifurcating arm portion 62 to the rear side thereof.

The treatment electrode 61 is elongated and wire-shaped. The bifurcating arm member 62 has a parallel portion in the inserting axis of the scope 12. Both end portions of the treatment electrode 61 are connected to a distal end portion of the bifurcating member. The processing electrode 61 is arc-shaped.

Further, the treatment electrode 61 and the bifurcating arm member 62 are hook-shaped at the distal end of the electrode unit 14 as an active electrode, and a predetermined angle is set between the plane including the arc treatment electrode 61 and the inserting axis of the scope 12.

The outer periphery of the metal pipe 63 is covered with an insulating tube (not shown), and a proximal portion of the metal pipe 63 is exposed to the rear end portion of the insulating tube as an electrode connecting portion.

The electrode unit 14 having a function of the active electrode is arranged in the inner sheath 31 so that the treatment electrode 61 can advance and retract in the inserting direction of the inner sheath 31 at the opening portion 35 of the distal end member 34 thereof.

The proximal portion of the metal pipe 63 having the treatment electrode 61 and the bifurcating arm member 62 on the distal end side thereof is inserted in the inserting portion 32 and the proximal main body portion 33 of the inner sheath 31, is extended from the base end surface of the proximal main body portion 33, and is fixed to a slider 46 which will be described later.

The handle portion 13 mainly comprises a sheath connecting portion 47 which is detachably connected to the proximal main body portion 33 of the inner sheath 31, a guide tube 48 which protrudes from the rear end surface of the sheath connecting portion 47 rearward and in which the inserting tube 41 is inserted, and the substantially pipe-shaped slider 46 to which the guide tube 48 is slidably held.

The slider 46 comprises an electrode fixing portion (not shown) as an electrically connecting portion to the electrode connecting portion at the rear end portion of the electrode unit 14, a connector 49 for high-frequency power supply to which the cable 5 for the power supply extended from the high-frequency power supply device 2 is detachably connected, and a thumb-hook ring 50 which is ring-shaped and to which the operator's thumb is hooked.

The slider 46 and the sheath connecting portion 47 are connected by an elastic member such as a spring (not shown) so that they are energized to be away from each other. That is, the slider 46 is always energized to the ocular portion 44 by the elastic member.

The operator properly reduces the distance between a finger hook portion 51 of the sheath connecting portion 47 and the ring 50 while gripping the finger hook portion 51 and the thumb-hook ring 50 arranged to the slider 46, thereby moving the slider 46 in the direction of the distal end of the scope 12 with respect to the guide tube 48. The treatment electrode 61 in the electrode unit 14 moves to be projected in the distal end direction of the inserting tube 41.

When no force acts to the finger-hook portion 51 and the ring 50, the treatment electrode 61 and the distal end portion of the inserting tube 41 are at substantially the same position in the inserting direction of the scope 12. However, when the force acts to the finger-hook portion 51 and the ring 50 in a direction shown by an arrow a in FIG. 4 to reduce the distance, the inserting tube 41 does not move but the treatment electrode 61 moves in a direction shown by an arrow b in FIG. 4 so that it is projected in the distal end direction of the scope 12.

The connector 49 for supplying the high-frequency power is electrically connected to the electrode fixing unit by, e.g., lead wiring. Thus, the cable 5 connected to the high-frequency power supply device 2 is connected to the connector 49 for supplying the high frequency so that it is energized to the treatment electrode 61 in the electrode unit 14 for the treatment of the lesion portion.

The resectoscope apparatus measures leak current by obtaining the difference between the current value supplied to the treatment electrode 61 and the current value of the return current.

Figure 5:
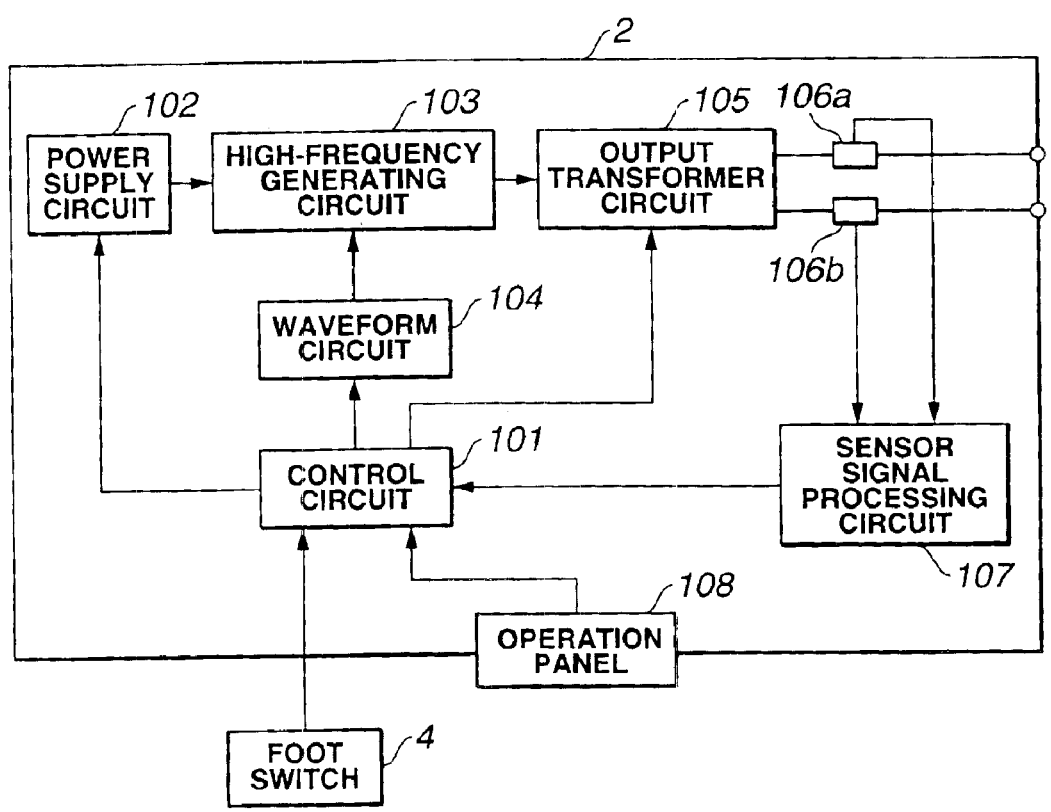

FIG. 5 is a block diagram showing an inner structure of the high-frequency power supply device 2.

Referring to FIG. 5, the high-frequency power supply device 2 comprises a control circuit 101 for receiving a signal from the foot switch 4 and for controlling the power supply, a power supply circuit 102 for generating DC power under the control of the control circuit 101, a high-frequency generating circuit 103 for switching DC current from the power supply circuit 102 and for generating high-frequency power, a waveform circuit 104 for supplying a waveform signal with the high-frequency current generated by the high-frequency generating circuit 103 under the control of the control circuit 101 to the high-frequency generating circuit 103, an output transfer circuit 105 for amplifying a high-frequency voltage with the high-frequency power generated by the high-frequency generating circuit 103, for applying the amplified voltage between a terminal for the treatment electrode 61 and a terminal for the return current, and for supplying the high-frequency current to the treatment current 61, current sensors 106a and 106b for detecting the high-frequency current outputted from the output transfer circuit 105, and a sensor signal processing circuit 107 for A/D converting the current values detected by the current sensors 106a and 106b. The control circuit 101 controls the power supply circuit 102 and the waveform circuit 104 based on digital current data from the sensor signal processing circuit 107.

A specific description is given of a collecting mechanism (collecting means) for collecting the return current in the above resectoscope apparatus. According to the first embodiment, the return current is collected without using the counter-electrode plate in the related art. The collecting means or method includes a plurality of ones.

(1) Collection of the Return Current Via the Outer Sheath

Figure 6:
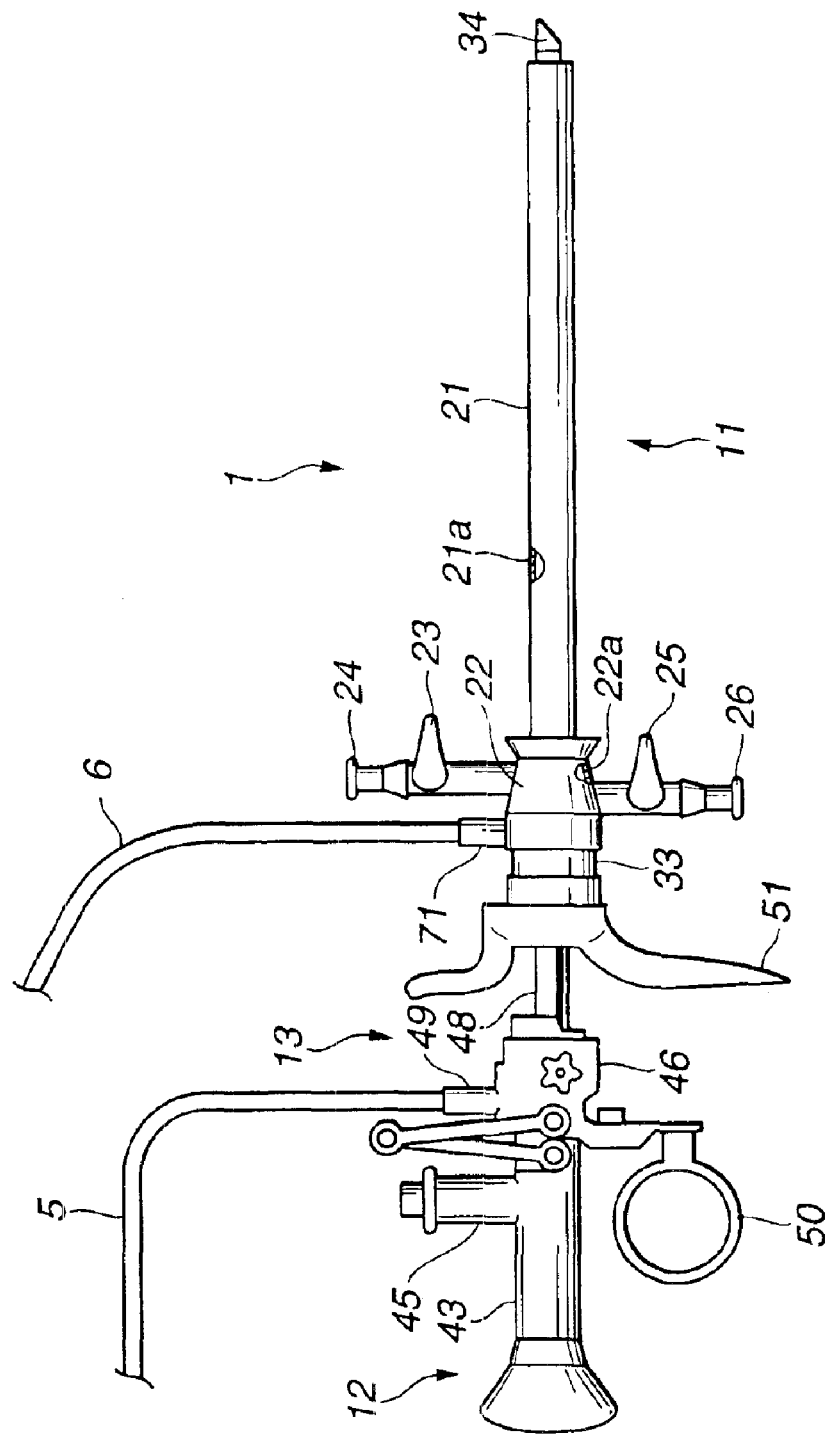

FIG. 6 shows the structure of the resectoscope 1 having a connector for connection to the cable for the return current at the proximal portion of the outer sheath.

Referring to FIG. 6, a cable connector 71 for the return current is arranged to the proximal main body portion 22 of the outer sheath 11. The connector 71 is fixed to the outer sheath 11 and, however, it may be detachable to the outer sheath 11.

In this case, the inserting portion 21 and the proximal main body portion 22 of the outer sheath 11 are made of a conductive member such as a metal member, e.g., stainless steel (shown by reference numerals 21a and 22a). Since the inserting portion 21 and the proximal main body portion 22 are the conductive member, the current from the active electrode flows to the outer sheath 11 via the conductive solution and further flows to the connector 71 as electrically connecting means to the cable 6 for the return current. Therefore, the return current is collected to the cable 6 for the return current via the outer sheath 11.

In this case, when the return current is collected via the outer sheath, if the body organ touches the outer sheath 11, the return current is collected via the metal members 21a and 22a due to the difference in impedance.

With the above structure, the return current is collected without the arrangement of the return electrode near the distal end portion of the sheath in the related art. Consequently, the structure of the resectoscope is simple, the inserting portion is made thin in diameter, and the resectoscope is smoothly inserted in the urethra.

(2) Collection of the Return Current Via the Inner Sheath (First Modification)

Figure 7:
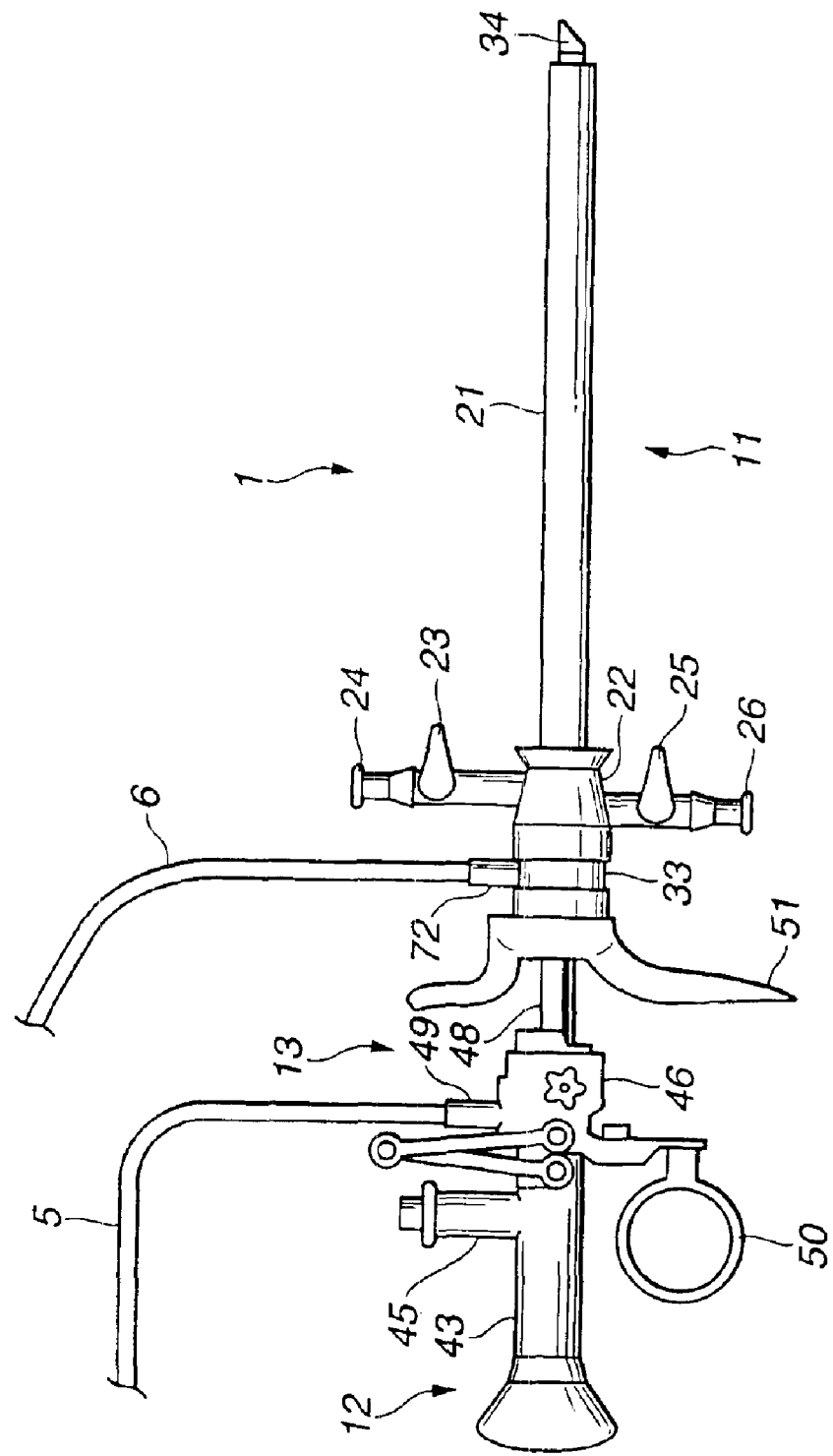

Next, a first modification will be described. FIG. 7 shows the structure of the resectoscope 1 having a connector for the connection to the cable for the return current at the proximal portion of the inner sheath.

According to the first modification, referring to FIG. 7, a cable connector 72 for the return current is arranged to the proximal main body portion 33 of the inner sheath 31. The connector 72 is fixed to the inner sheath 31, however, it may be detachable to the inner sheath 31.

In this case, the inserting portion 32 and the proximal main body portion 33 in the inner sheath 31 are made of a conductive member such as metal. Thus, the current from the active electrode flows to the inner sheath 31 via the conductive solution and further flows to the connector 72 as electrically connecting means to the cable 6 for the return current. Therefore, the return current is collected to the cable 6 for the return current via the inner sheath 31.

With the above structure, the return current is collected without the arrangement of the return electrode near the distal end portion of the sheath in the related art. Consequently, the structure of the resectoscope is simple, the inserting portion is made thin in diameter, and the resectoscope is smoothly inserted in the urethra.

(3) Collection of the Return Current Via the Scope (Second Modification)

Figure 8:
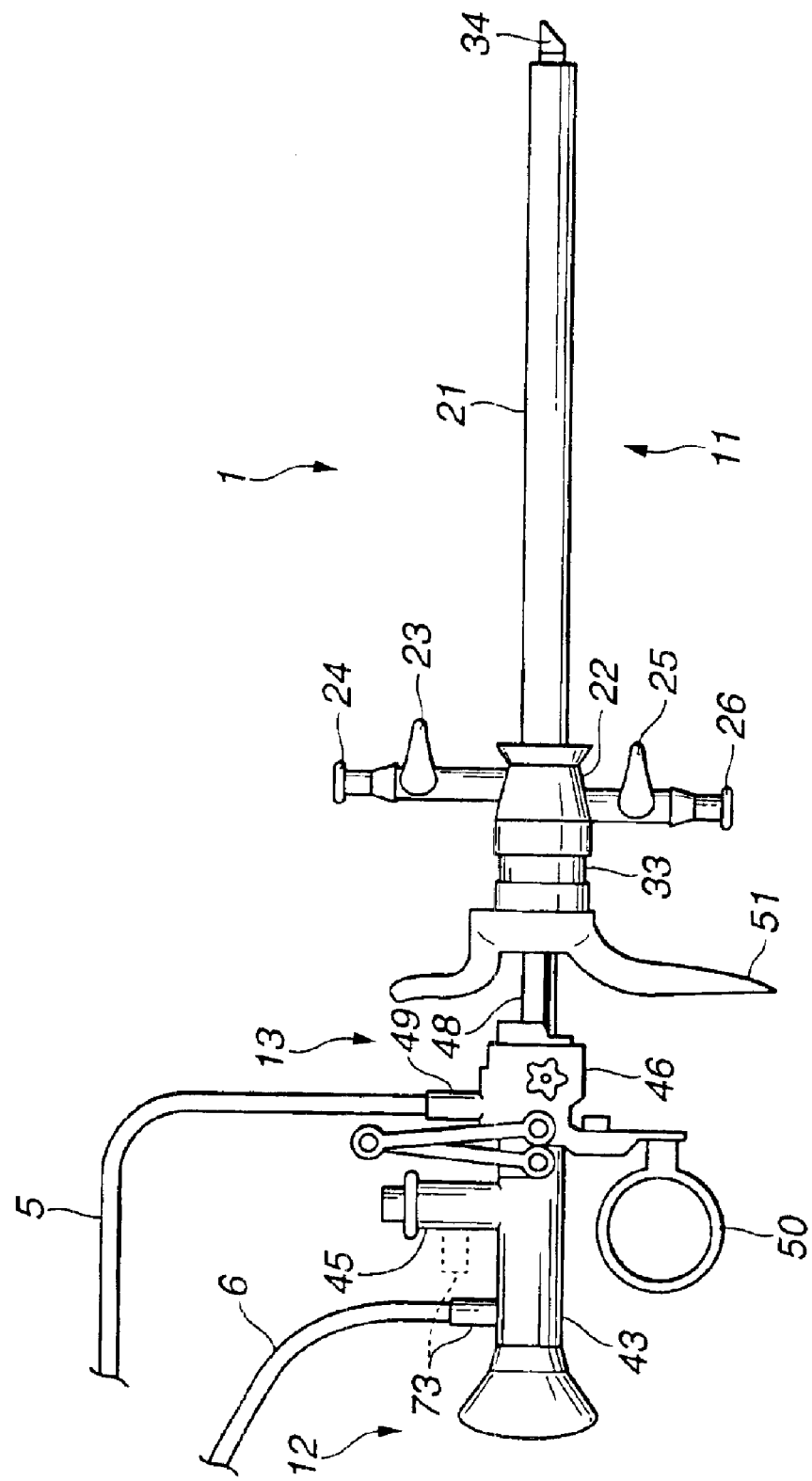

Next, a second modification will be described. FIG. 8 shows the structure of the resectoscope 1 having a connector for the connection to the cable for the return current at the proximal portion of the scope.

According to the second modification, referring to FIG. 8, a cable connector 73 for the return current is arranged to the proximal portion 43 of the scope 12. The connector 73 is fixed to the scope 12, however, it may be detachable to the scope 12.

In this case, the guide tube 42, the sheath connecting portion 47, the guide tube 48, the slider 46, and the proximal portion 43 are made of the conductive member such as metal. The current from the active electrode flows to the scope 12 via the conductive solution and further flows to the connector 73 as electrically connecting means to the cable 6 for the return current. Therefore, the return current is collected to the cable 6 for the return current via the scope 12.

With the above structure, the return current is collected without the arrangement of the return electrode near the distal end portion of the sheath in the related art. Consequently, the structure of the resectoscope is simple, the inserting portion is made thin in diameter, and the resectoscope is smoothly inserted in the urethra.

As shown by a dotted line in FIG. 8, the connector 73 may be arranged to the light guide connecting portion 45 of the scope 1.

(4) Collection of the Return Current Via the Handle Portion (Third Modification)

Figure 9:
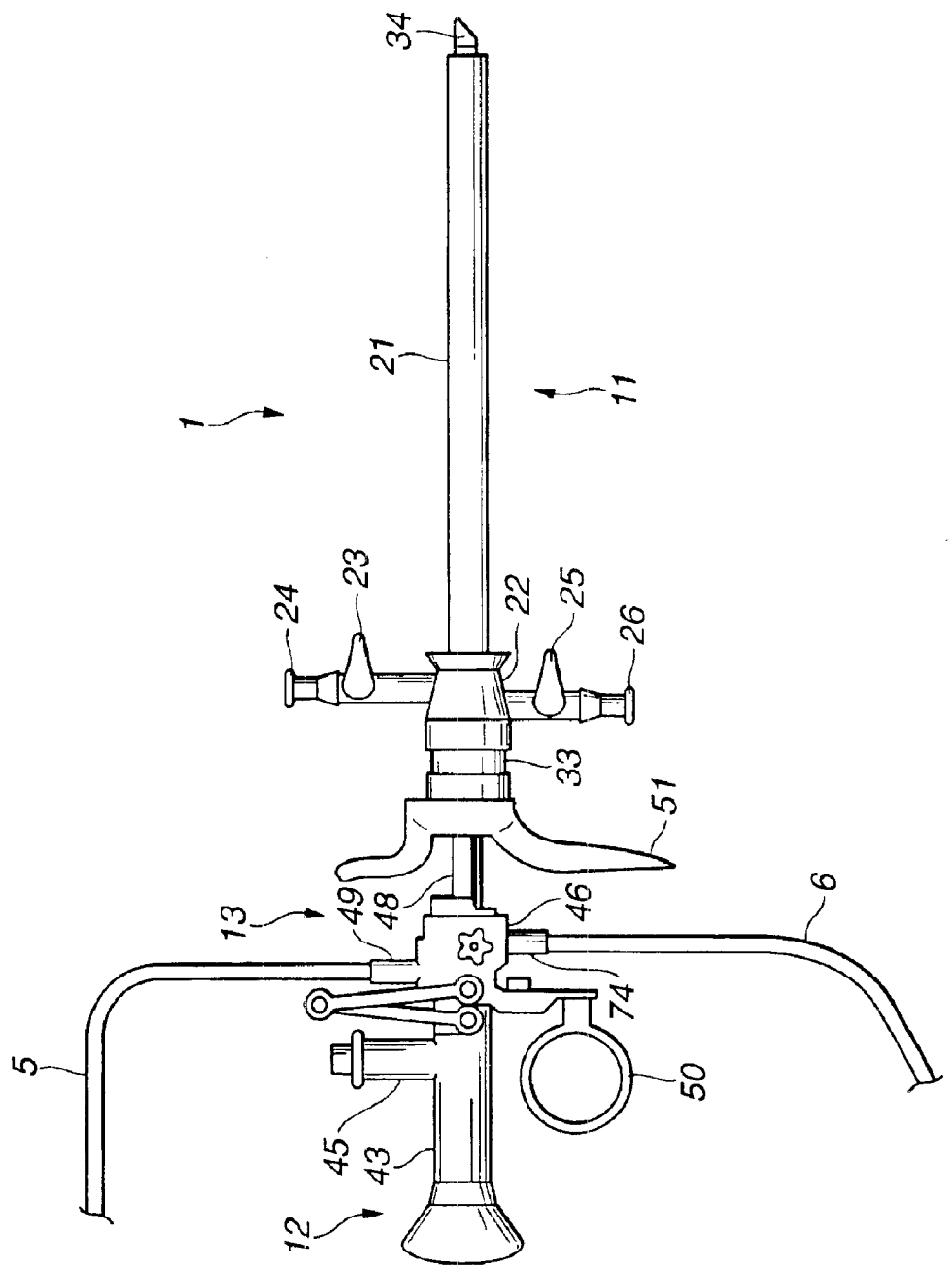

Next, a third modification will be described. FIG. 9 shows the structure of the resectoscope 1 having a connector for the connection to the cable for the return current at the handle portion.

According to the third modification, referring to FIG. 9, a cable connector 74 for the return current is arranged to the slider 46 of the handle portion 13 as a holding member for holding the active electrode. The connector 74 is fixed to the handle portion 13, however, it may be detachable to the handle portion 13.

The connector 74 is electrically connected to the guide tube 48 as the conductive member such as the metal in the handle portion 13. Further, the guide tube 48 is electrically connected to the outer sheath 11, the inner sheath 31, or the scope 12.

Therefore, the current from the active electrode flows to the handle portion 13 via the outer sheath 11, the inner sheath 31, or the scope 12, and further flows to the cable 6 for the return current via the connector 74 as the electrically connecting means to the cable 6 for the return current. Therefore, the return current is collected to the cable 6 for the return current via the handle portion 13.

With the above structure, the return current is collected without the arrangement of the return electrode near the distal end portion of the sheath in the related art. Consequently, the structure of the electroscope is simple, the inserting portion is made thin in diameter, and the electroscope is smoothly inserted in the urethra.

Figure 10:
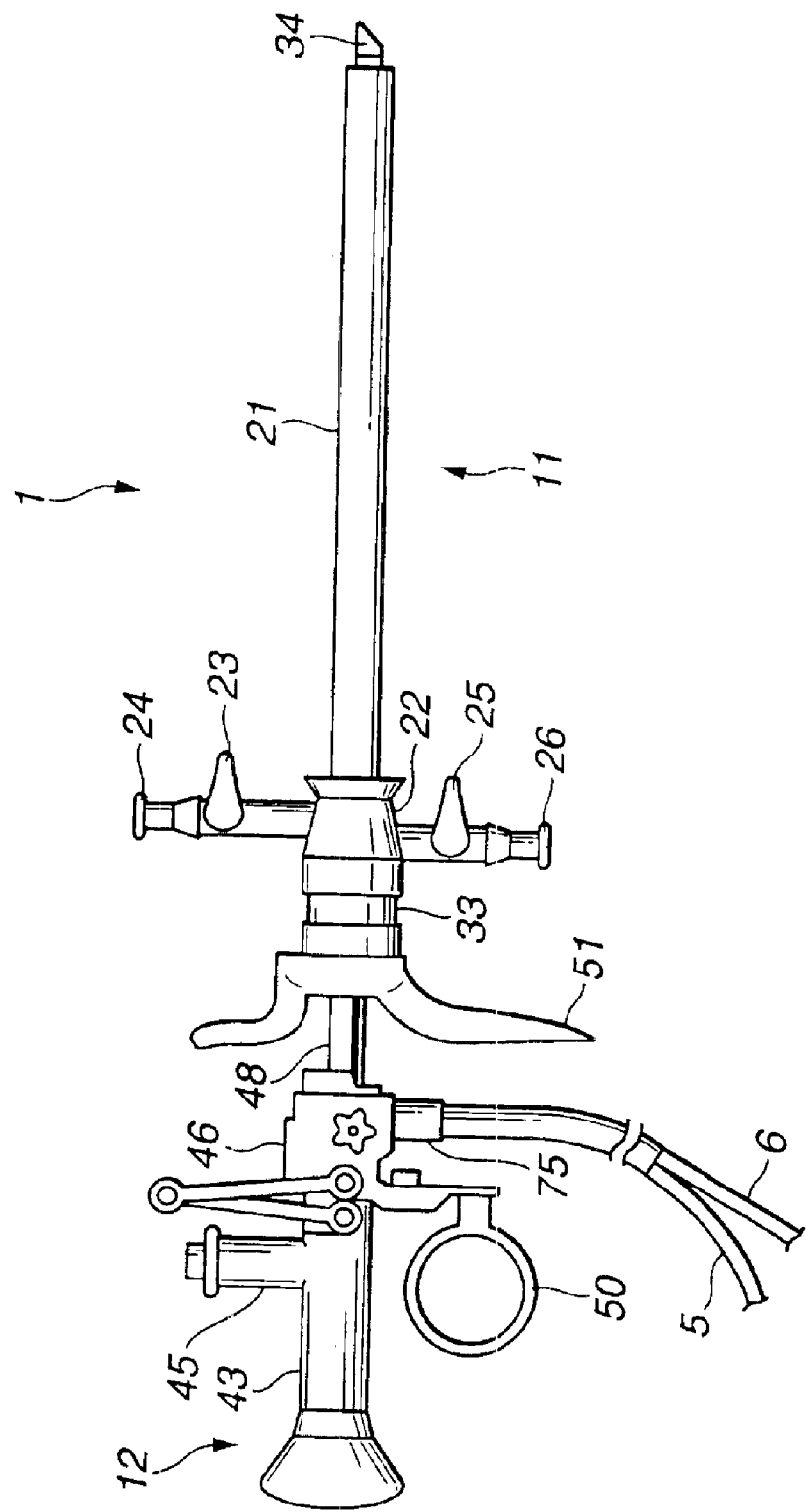

FIG. 10 is a side view showing the structure for supplying and collecting the active current and the return current by the individual cable in the single cable for each current. The single cable includes two cables of a cable for the active cable and a cable for the return cable.

The connector 75 is arranged to the slider 46. In the single connector 75, the two cables are connected to a connector portion for the active current and to a connector portion for the return current in the resectoscope 1. As a result, the cable for the active current and the cable for the return current are integrated and the connecting portion to the connector 75 is integrated, thereby improving the operability.

(5) Collection of the Return Current Via the Fluid Tube (Fourth Modification)

Figure 11:
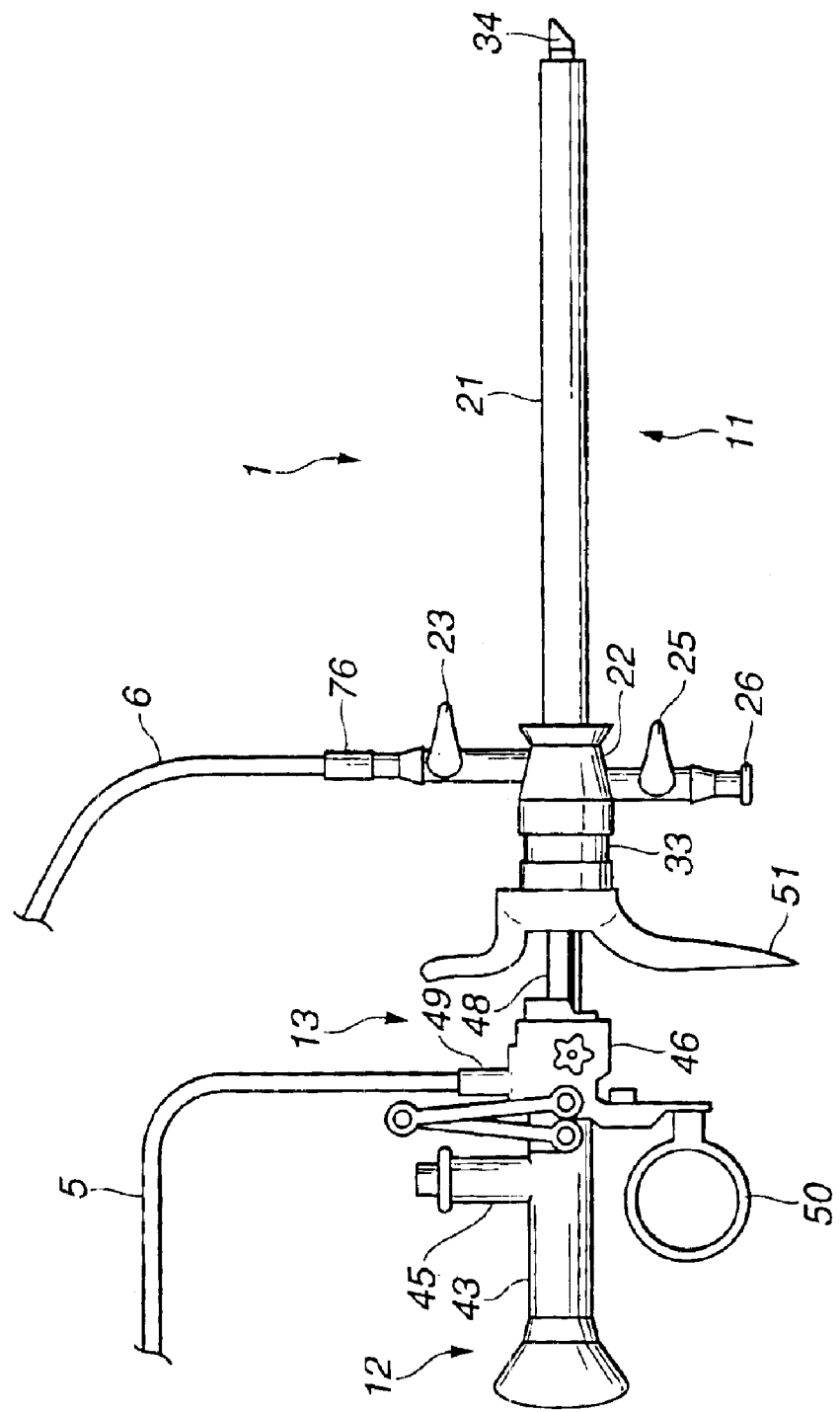

A fourth modification will be described. FIG. 11 shows the structure of the resectoscope 1 having a connector for connection to the cable for the return current at one side of the fluid tube.

According to the fourth modification, referring to FIG. 11, a cable connector 76 for the return current is arranged to the solution supply cap 24 provided on the outer sheath 11. The solution supply cap 24 is arranged at the distal end portion of the solution supply tube provided on the outer sheath 11. The connector 76 is fixed to the solution supply cap 24, however, it may be detachable to the solution supply cap 24.

In this case, the inserting portion 21, the proximal main body portion 22, and the fluid tube 22a are made of the conductive member such as metal. The current from the active electrode flows to the fluid tube 22a via the conductive solution and further flows to the connector 76 as the electrically connecting means to the cable 6 for the return current. Therefore, the return current is collected to the cable 6 for the return current via the fluid tube.

Figure 12:
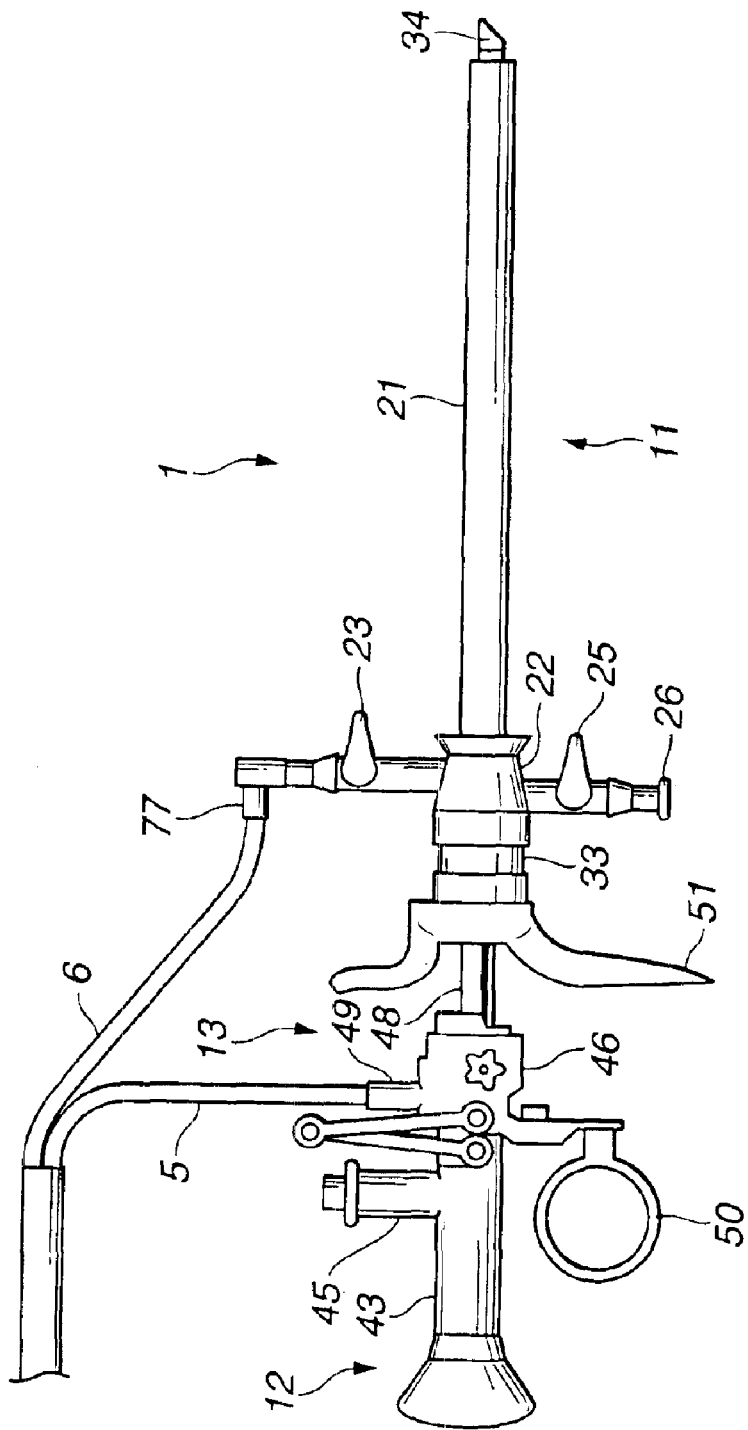

FIG. 12 is a side view showing the structure in which the connector 77 is projected from the side portion of the fluid tube 22a.

Although the solution supply cap 24 has the connectors 76 and 77, the solution drain cap 26 may have the connectors 76 and 77.

Further, although the connector is arranged to the solution supply cap 24 or the solution drain cap 26, independently, as mentioned above, the shape of the solution supply cap 24 or the solution drain cap 26 is not changed and either one may be used as the connector 76 for the return current so as to collect the return current.

With the above structure, the return current is collected without the arrangement of the return electrode near the distal end portion of the sheath in the related art. Consequently, the structure of the resectoscope is simple, the inserting portion is made thin in diameter, and the resectoscope is smoothly inserted in the urethra.

When the treatment using the conductive solution is performed by using the resectoscope apparatus having the connector for connection to the cable for the return current as described above, the cable 6 for the return current may be connected to the connector arranged to the outer sheath or the like as shown in FIG. 1.

Figure 13:
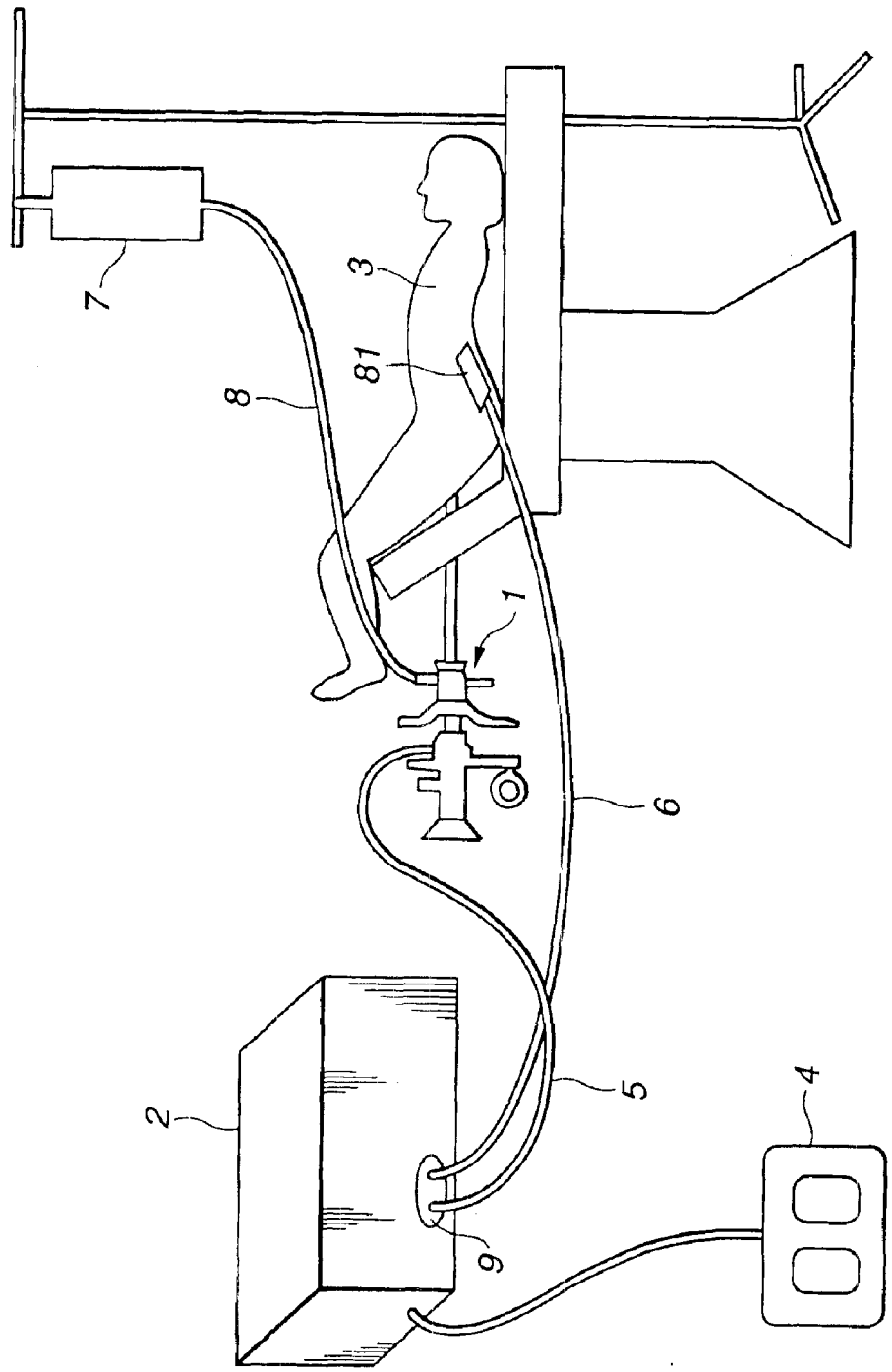

Further, the cable for the return current is not connected to the connector for connection, the resectoscope apparatus can be used for the treatment using non-conductive solution. In this case, a usually used counter-electrode plate 81 is adhered to the body of the patient 3 as shown in FIG. 13 and the counter-electrode plate 81 may be connected to the cable 6 for the return cable. FIG. 13 is a diagram for explaining a status in which the treatment is executed by adhering the counter-electrode plate to the body of the patient.

Hence, the resectoscope apparatus having the connector for connection to the cable for the return cable can be used for the treatment using the conductive solution and, further, can be used for the treatment using the non-conductive solution.

Figure 14:
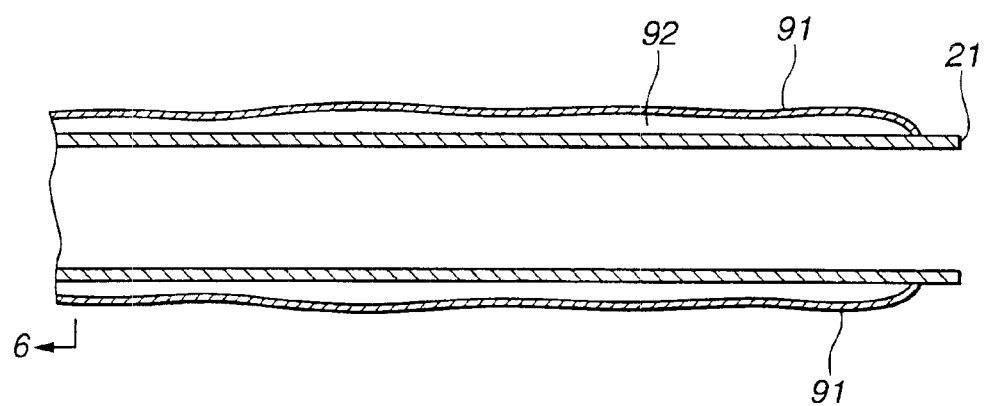

The certain collection of the return current without using the counter-electrode plate needs to increase a contact area with the body organ. FIG. 14 is a diagram showing the structure in which a conductive balloon, namely, a pouch member is provided at the outer periphery of the inserting portion 21 to increase the contact area upon the treatment using no conductive solution and thus the adhesiveness to the body organ of the celom is improved.

Referring to FIG. 14, a pouch member 91 made of a conductive material such as metal mesh is provided to package the inserting portion 21. That is, pouch means is an elastic soft member made of a conductive member.

The pouch member 91 has an air intake slit (not shown) for supplying air into an inner portion 92 of the pouch member 91 and for expanding the pouch member from one end thereof. The pouch means 91 is expanded by supplying the air to the inner portion 92 from an air supply device (not shown) via the air intake slit.

Further, the pouch member 91 is electrically connected to the cable 6 for the return current. Fluid other than the air may be supplied to the inner portion 92.

With the above structure, since the pouch member 91 is conductive, the adhesiveness between the body organ and the pouch member 91 is improved around the inserting portion 21 by supplying the air or the like to the inner portion 92 to expand the pouch member 91. Therefore, in the case of using the resectoscope according to the first embodiment for the treatment using the non-conductive solution, the return current is accurately collected without using the counter-electrode plate as the conventional return electrode.

The return current may be collected from the pouch member 91 via the inner sheath, outer sheath, scope, or handle portion by electrically connecting the pouch member 91 to the inner sheath, outer sheath, scope, or handle portion by using the electrically connecting means such as the cable.

According to the first embodiment, the resectoscope apparatus can be realized in which both the treatment using no conductive solution and the treatment using the conductive solution can be used without making the diameter of the inserting portion thick.

With the above structure, in the case of using the conductive solution, it is possible to realize the resectoscope apparatus in which the structure is simple and the return current is easily collected.

A second embodiment of the present invention will be described with reference to FIGS. 15 to 17. According to the second embodiment, the resectoscope apparatus is realized in which the treatment is performed by the output characteristic of the proper high-frequency current in both cases of the treatment using the non-conductive solution and of the treatment using the conductive solution, by calculating the impedance between the active electrode and the return electrode, that is, impedance of the body organ including the solution.

Figure 15:
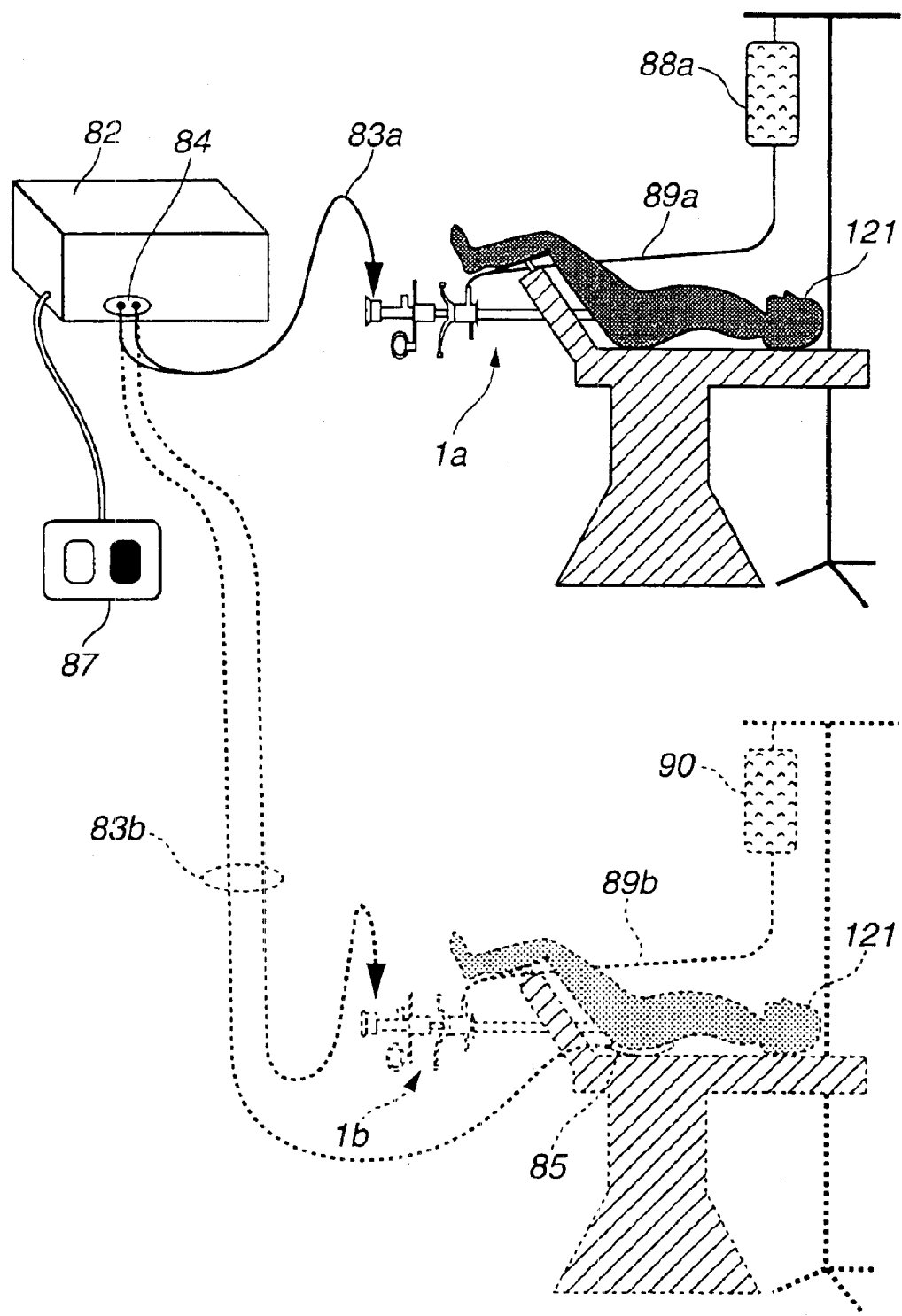

FIG. 15 shows a status for transurethral resection using the resectoscope apparatus.

The resectoscope apparatus comprises a resectoscope 1a for the conductive solution or a resectoscope 1b for the non-conductive solution, and a high-frequency power supply device 82.

In the resectoscope 1a for the conductive solution, a connector 84 of the high-frequency power supply device 82 can be connected to a cable 83a which supplies high-frequency current (hereinafter, referred to as active current) and which collects return current, to/from a treatment electrode arranged to the distal end thereof.

In the resectoscope 1b for the non-conductive solution, the connector 84 of the high-frequency power supply device 82 is connected to a cable 83b which supplies the active current to the treatment electrode arranged to the distal end thereof and which collects the return current via a counter-electrode plate 85 arranged to the body surface of a patient 121.

The distal end portion of the resectoscope 1a for the conductive solution or the resectoscope 1b for the non-conductive solution is transurethrally inserted in the patient 121. A foot switch 87 connected to the high-frequency power supply device 82 is switched on or off to control the power supply to the treatment electrode of the resectoscope 1a for the conductive solution or the resectoscope 1b for the non-conductive solution from the high-frequency power supply device 82.

The foot switch 87 is turned on and thus the high-frequency current from the high-frequency power supply device 82 is supplied to the treatment electrode of the resectoscope 1a for the conductive solution via the cable 83a and the return current is collected to the high-frequency power supply device 82. Or, similarly, the foot switch 87 is turned on and thus the high-frequency current from the high-frequency power supply device 82 is supplied to the treatment electrode of the resectoscope 1b for the non-conductive solution via the cable 83b and the return current is collected to the high-frequency power supply device 82 via the counter-electrode plate 85.

Referring to FIG. 15, in the resectoscope 1a for the conductive solution, physiological saline with the conductivity as perfusate is supplied to the celom such as the bladder from a physiological saline pack 88a via a sterilizing tube 89a. In the resectoscope 1b for the non-conductive solution, non-conductive solution as perfusate is supplied to the celom such as the bladder from a non-conductive solution pack 90 via a sterilizing tube 89b.

The operator fills the celom with the solution, then inserts into the celom, the resectoscope 1a for the conductive solution or the resectoscope 1b for the non-conductive solution to the celom, moves the treatment electrode to the surface of the body organ for the incision and resection while viewing the endoscope image for observing, and turns on a switch of the foot switch 87 for the incision.

Figure 16:
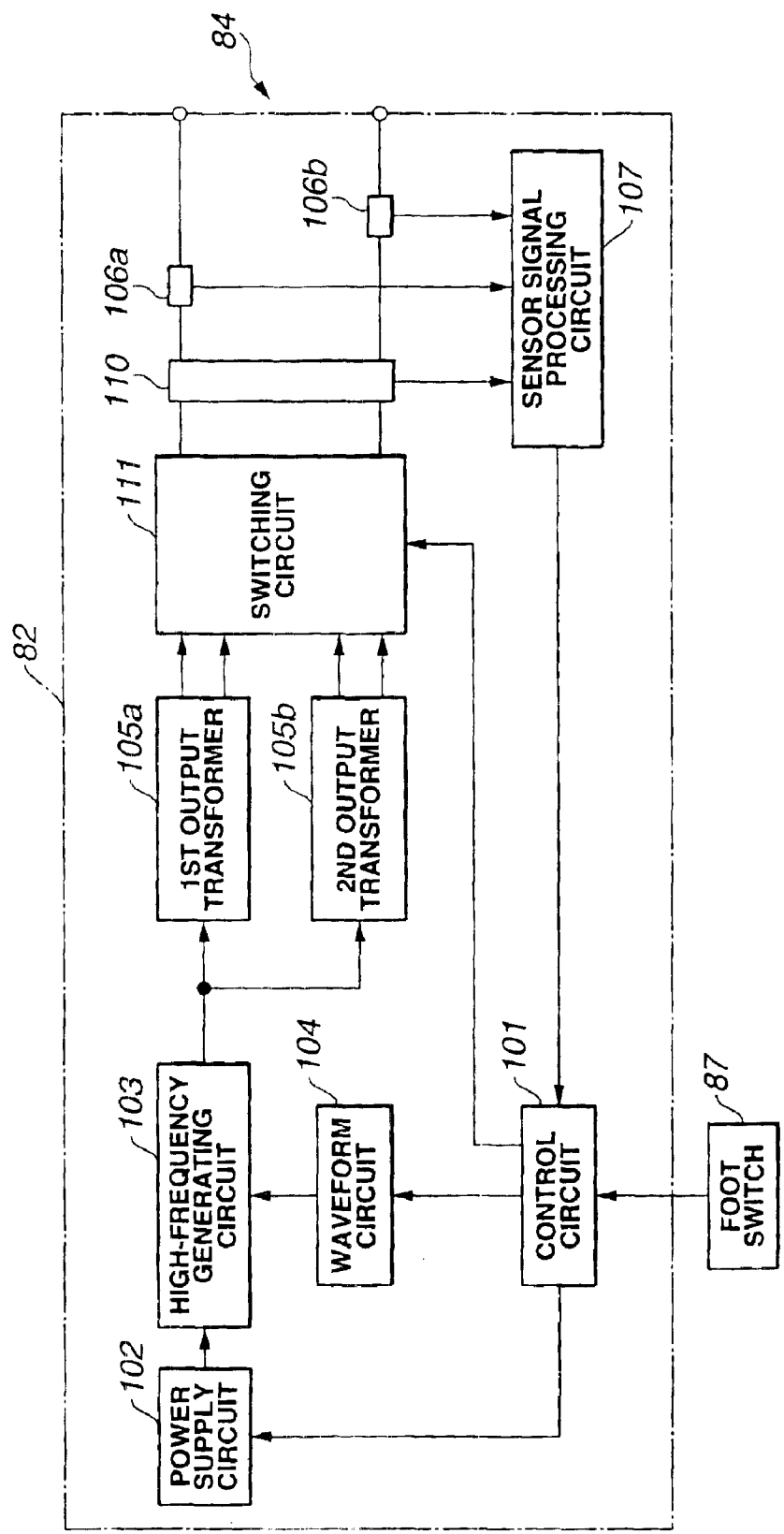

Referring to FIG. 16, the high-frequency power supply device 82 comprises a control circuit 101 for receiving a signal from the foot switch 87 and for controlling the power supply, a power supply circuit 102 for generating DC power under the control of the control circuit 101, a high-frequency generating circuit 103 for switching the DC current from the power supply circuit 102 and for generating high-frequency power, a waveform circuit 104 for supplying a waveform signal with the high-frequency current generated by the high-frequency generating circuit 103 under the control of the control circuit 101 to the high-frequency generating circuit 103, a first output transfer circuit 105a for outputting the high-frequency power of a first output characteristic which is obtained by amplifying a high-frequency voltage with the high-frequency power generated by the high-frequency generating circuit 103 and for supplying the amplified high-frequency current to the resectoscope 1a for the conductive solution, a second output transfer circuit 105b for outputting the high-frequency power of a second output characteristic which is obtained by amplifying a high-frequency voltage with the high-frequency power generated by the high-frequency generating circuit 103 and for supplying the amplified high-frequency current to the resectoscope 1b for the non-conductive solution, a switching circuit 111 which switches the output from the first output transfer circuit 105a and the output from the second output transfer circuit 105b and which outputs the switched output to the connector 84, a voltage sensor 110 for detecting the voltage of the high-frequency output outputted from the switching circuit 111, current sensors 106a and 106b for detecting the high-frequency current outputted from the switching circuit 111, and a sensor signal processing circuit 107 for A/D converting the voltage value detected by the voltage sensor 110 and the current values detected by the current sensors 106a and 106b.

The control circuit 101 calculates the impedance of the body organ based on digital voltage data and digital current data from the sensor signal processing circuit 107 and controls the power supply circuit 102 and the waveform circuit 104.

The foot switch 87 is switched on and the control circuit 101 supplies minute high-frequency current from the connector 84 to the resectoscope 1a for the conductive solution or the resectoscope 1b for the non-conductive solution. The minute high-frequency current is detected by the voltage sensor 110, and the current sensors 106a and 106b, and the sensor signal processing circuit 107 A/D converts the voltage value detected by the voltage sensor 110 and the current values detected by the current sensors 106a and 106b. The control circuit 101 calculates the impedance of the body organ including the solution from the voltage value and the current values from the sensor signal processing circuit 107.

Figure 17:
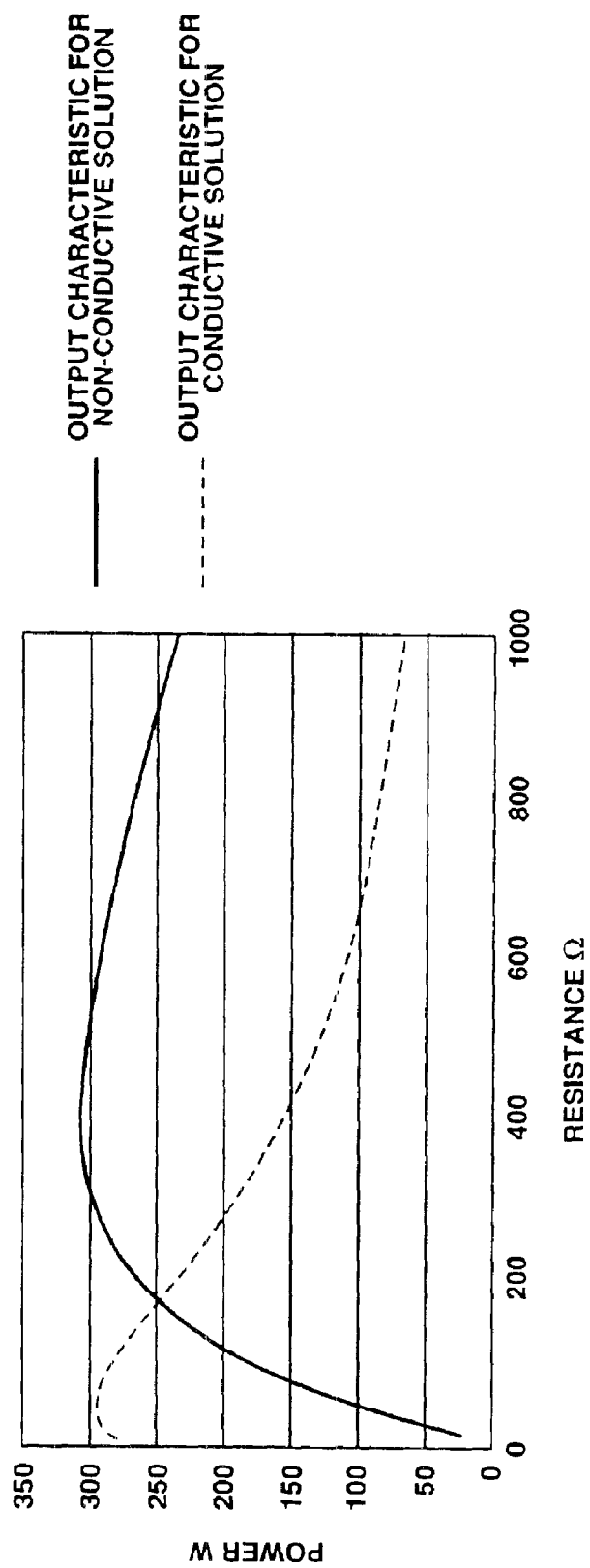

Referring to FIG. 17, the high-frequency output from the first output transfer circuit 105a is an output with an output characteristic for the conductive solution indicating the maximum power at approximately 50 Ω, and the high-frequency output from the second output transfer circuit 105b is an output with an output characteristic for the non-conductive solution indicating the maximum power at approximately 300 Ω.

The control circuit 101 controls the switching circuit 111 based on the calculated impedance and outputs to the connector 84, the high-frequency output with the output characteristic in accordance with the connected resectoscope.

According to the second embodiment, since the impedance of the body organ including the solution is calculated and the switching circuit 111 is switched based on the calculated impedance, the high-frequency current with the best output characteristic is certainly supplied depending on the resectoscope.

The present invention is not limited to the above embodiments and can variously be modified without departing from the scope of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A resectoscope apparatus comprising:
   a high-frequency generating device which generates high-frequency current;
   a hollow sheath which can be inserted in the celom;
   a scope having an inserting tube which is arranged in the sheath and which can observe the celom, the scope having at least a conductive portion;
   an active electrode which transmits the high-frequency current to the body organ;
   an operating portion for moving the active electrode relative to the inserting tube, the operating portion being electrically connected to the conductive portion of the scope;
   a solution supply device which supplies a solution to the hollow sheath; and
   a connecting member provided to the operating portion for connection to the high frequency generating device which uses the conductive portion of the scope as a member for collecting return current.

2. A resectoscope apparatus according to claim 1, wherein the high-frequency generating device comprises an impedance measuring circuit which measures the impedance between the active electrode and the connecting member.

3. A resectoscope apparatus according to claim 1, wherein the high-frequency generating device comprises:
   an impedance measuring circuit which measures the impedance between the active electrode and the connecting member; and
   a control circuit which controls an output characteristic of the high-frequency current based on a measuring result of the impedance measuring circuit.

4. A resectoscope apparatus according to claim 1, wherein the solution supply device supplies a conductive solution with conductivity.

5. An electrical operation method using a resectoscope, the method comprising:
   guiding a scope into a celom, the scope having an observation optical system at an inserting tube via a sheath which is inserted into the celom, the scope further having an active electrode;
   transmitting high-frequency current to the body organ via the active electrode; and
   collecting return current to a high-frequency generating device from an operating portion for moving the active electrode via a conductive portion of the scope.

6. A resectoscope comprising:
   a hollow sheath which can be inserted in the celom;
   a scope which is arranged in the sheath and which observes the celom, the scope having at least a conductive portion;
   an active electrode which is arranged in the sheath and which transmits high-frequency current to the body organ;
   an operating portion for moving the active electrode relative to the inserting tube, the operating portion being electrically connected to the conductive portion of the scope;
   a tube connecting portion which connects a tube to which a solution is supplied from a solution supply device; and
   a connecting portion for return current which is provided to the operating portion and which collects return current of the high-frequency current using the conductive portion of the scope.

7. A resectoscope according to claim 6, wherein the scope comprises an inserting tube having an observation optical system for observing the celom and a guide tube for inserting the inserting tube therein, and wherein the operating portion is electrically connected to the guide tube and collects return current via the guide tube.

8. A resectoscope according to claim 6, further comprising a connecting portion for supplying high-frequency current which is provided to the operating portion and which transmits high-frequency current to the body organ via the active electrode.

* * * * *